US006846640B2

(12) United States Patent
Peach et al.

(10) Patent No.: US 6,846,640 B2
(45) Date of Patent: Jan. 25, 2005

(54) TIME-RESOLVED FLUORESCENCE ASSAY FOR THE DETECTION OF MULTIMERIC FORMS OF A-BETA 1-40

(75) Inventors: Matthew L. Peach, Portage, MI (US); Alice L. Laborde, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 27 days.

(21) Appl. No.: 10/135,592

(22) Filed: Apr. 30, 2002

(65) Prior Publication Data

US 2003/0203403 A1 Oct. 30, 2003

(51) Int. Cl.$^7$ ........................ G01N 33/53; G01N 33/533
(52) U.S. Cl. .................. 435/7.1; 435/7.2; 435/500
(58) Field of Search ...................... 435/7.1, 7.2, 500

(56) References Cited

U.S. PATENT DOCUMENTS

| 5,721,106 | A | 2/1998 | Maggio et al. |
| 5,817,626 | A | 10/1998 | Findeis et al. |
| 5,837,473 | A | 11/1998 | Maggio et al. |
| 5,854,215 | A | 12/1998 | Findeis et al. |
| 6,319,498 | B1 | 11/2001 | Findeis et al. |

FOREIGN PATENT DOCUMENTS

| WO | WO 98/08868 | 3/1998 |
| WO | WO 99/06545 | 2/1999 |
| WO | WO 99/06838 | 2/1999 |

OTHER PUBLICATIONS

Ross (Aug. 29, 2002) "Polyglutamine pathogenesis: emergence of unifying mechanisms for Huntington's diseases and related disorders." Neuron 35(5):819–822.*
Tobin & Signer (Dec. 2000) "Huntington's disease: the challenge for cell biologists." Trends Cell Biol. 10(12):531–536.*
Sipe (1992) "Amyloidosis" Annu. Rev. Biochem. 61: 947–975.*
Akikusa et al., "Practical assay and molecular mechanism of aggregation inhibitors of β–amyloid," *J. Pept. Res.*, 61:1–6 (2003).
Hetenyi et al., "Pentapeptide Amides Interfere with the Aggregation of β–Amyloid Peptide of Alzheimer's Disease," *Biochemical and Biophysical Research Communications*, 292:931–936 (2002).

Howlett et al., "Inhibition of fibril formation in β–amyloid peptide by a novel series of benzofurans," *Biochem. J.*, 340:283–280 (1999).
Hughes et al., "β2–macroglobulin associates with β–amyloid peptide and prevents fibril formation," *Proc. Natl. Acad. Sci. USA*, 95:3275–3280 (1998).
Watanabe et al., "Inhibitors of Fibril Formation and Cytotoxicity of β–Amyloid Peptide Composed of KLVFF Recognition Element and Flexible Hydrophilic Disrupting Element," *Biochemical and Biophysical Research Communications*, 290:121–124 (2002).
Allsop et al., *Biochem. Biophy. Res. Comm.*, 285:58–63 (2001).
Azriel et al., *J. Biol. Chem.*, 276:34156–161 (2001).
Berthelier et al., *Anal. Biochem.*, 295:227–236 (2001).
Cane et al., *Science*, 282:63–68 (1998).
Citron et al., *Nature*, 360:672–674 (1992).
Davies P., *Annals of the N.Y. Acad. of Sci.*, 924:8–16 (2000).
Findeis et al., *Biochemistry,* 38:6791–6800 (1999).
Haas et al., *Nature*, 359:322–325 (1992).
Howlett et al., *FEBS Letters*, 417:249–251 (1997).
Iwatsubo et al., *Neuron.*, 13:45 (1994).
Kang et al., *Nature*, 325:733–736 (1987).
Kitaguchi et al., *Nature*, 331:530–532 (1988).
Lannfelt et al., *Neurosci. Lett.*, 153:85–87 (1993).
Lowe et al., *Biochemistry*, 40:7882–89 (2001).
Myers, *Curr. Opin. Biotechnol.*, 8:701–707 (1997).
Perutz and Windle, *Nature*, 412:143–144 (2001).
Ponte et al., *Nature*, 331:525–527 (1988).
Schenk et al., *Nature*, 400:173–177 (1999).
Seubert et al., *Nature*, 359:325–327 (1992).
Tanzi et al., *Nature*, 331:528–530 (1988).
Yan et al., *Nature*, 402:533–537 (1999).

* cited by examiner

*Primary Examiner*—Elizabeth Kemmerer
*Assistant Examiner*—Christopher James Nichols
(74) *Attorney, Agent, or Firm*—Pharmacia & Upjohn Company; Thomas A. Wootton (57) ABSTRACT

The present invention provides for a polypeptide aggregation screening assay for the purpose of detecting modulators of polypeptide aggregation, which can provide for new therapies in pathologic states associated with polypeptide aggregation, especially considered is Alzheimer's Disease.

7 Claims, 2 Drawing Sheets

TIME-RESOLVED FLUORESCENCE ASSAY FOR THE DETECTION OF MULTIMERIC FORMS OF A-BETA 1-40

FIELD OF THE INVENTION

The present invention relates to methods of detection of modulators of polypeptide aggregation observed in many human disease states.

BACKGROUND OF THE INVENTION

A number of serious diseases affecting the human population can be closely associated with the improper aggregation of polypeptide fragments and characterized by aggregate deposition in lesions or plaques often resulting in abnormal physiological function at the plaque site. For instance, a stretch of polyglutamine repeats in a particular protein has been proposed as the cause for many neurological disorders including Huntington's disease and spinal bulbar muscular atrophy, while aggregation of other unrelated proteins are cited as the causes of prion disease (PrP aggregation), Parkinson's disease and amyotrophic lateral sclerosis (ALS) ($\alpha$-synuclein aggregation), dialysis-related amyloidosis ($\beta$-2 microglobulin aggregation), corneal dystrophy (kerato-epithelial deposits), and aggregation of islet amyloid polypeptide in more than 95% of type II diabetes. Of particular interest is the aggregation of $\beta$-amyloid polypeptides in Alzheimer's Disease.

Alzheimer's disease (AD) is a neurodegenerative disorder characterized by the gradual decline of cognitive function and memory loss associated with amyloid plaque formation, neurofibrillary tangles, and associated neuronal toxicity. The initiation and onset of Alzheimer's disease is believed to have both genetic origins as well as sporadic, environmentally influenced onset (Davies P., *Annals of the N.Y. Acad Of Sci.* 924: 8–16.2000). Several genetic mutations have been characterized to date that are associated with familial onset AD. Mutations which are significantly involved in AD onset have been found in the Amyloid Precursor Protein (APP) itself, and in either the presenilin-1 or presenilin-2 genes. However, the common denominator in all of these mutations is the formation of protein, or senile plaques derived from a cleavage fragment, designated amyloid beta (A$\beta$), of the APP molecule which is deposited in the brain of affected individuals, and results in toxicity and death of neuronal cells. This phenomenon of plaque formation can also be detected in another genetic defect not directly related to AD, the trisomy of chromosome 21 involved in Down's syndrome.

Amyloid precursor protein (APP), a single transmembrane glycoprotein possessing a large cytoplasmic domain and a short intracellular C-terminal region, occurs naturally as several splice forms of either 751 amino acids (Ponte et al., *Nature* 331: 525–527. 1988; Tanzi et al., *Nature* 331: 528–530. 1988), 770 amino acids (Kitaguchi et. al., *Nature* 331: 530–532. 1988), or 695 amino acids (Kang et. al., Nature 325: 733–736. 1987), designated as "normal" APP. The APP695 variant is more widely expressed in neurons.

Amyloid precursor protein cleavage takes place through a series of enzymatic reactions mediated by the $\alpha$, $\beta$, and $\gamma$ secretases. The $\alpha$-secretase cleaves ~12 residues N-terminal of the transmembrane domain of APP, at approximately residue 687 of APP770, generating the large soluble protein s-APP$\alpha$, which is nonpathogenic, and a C-terminal fragment of 83 amino acids. The $\gamma$-secretase cleaves after amino acid 711 or 712 in the C-terminal end to create a free peptide termed p3. Alternatively, APP can be cleaved N-terminal to the transmembrane domain before aspartyl residue 672 by $\beta$-secretase enzyme, a member of the aspartyl protease family of enzymes (Yan et al., *Nature* 402: 533–537. 1999), forming a truncated verison of sAPP$\alpha$, referred to as sAPP$\beta$. The remaining C-terminal fragment can also be cleaved by a $\gamma$-secretase, near residue 711, giving rise to soluble A$\beta$ peptide. The $\gamma$-secretase generates an A$\beta$ peptide of either 1-39, 1–40, 1-42, or 1–43 amino acids (where position 1 immediately follows the $\beta$-secretase cleavage site) depending upon its cleavage site. A$\beta$1-40 is the more abundant cleavage product produced by most cell types.

In addition to the formation of senile plaques by A$\beta$ fragments, A$\beta$ deposition can also be detected in nonfibrillar, granular associations termed diffuse plaques (Tagliavini et al., *Neurosci. Lett.* 93: 191). Diffuse A$\beta$ plaques are detectable in brains of normal, healthy individuals, while very few senile, amydyloidogenic plaques are detected in the brains of non-AD affected individuals. Antibody staining against A$\beta$ peptide revealed that the diffuse plaques are composed primarily of the highly amyloidogenic A$\beta$1-42 (Iwatsubo et al., *Neuron* 13:45. 1994) while senile plaques contain a mixture of both A$\beta$1-42 and A$\beta$1-40 peptides.

Several mutations of amyloid precursor protein that result in increased cleavage of APP into A$\beta$ peptides have been characterized. The "Swedish" mutation, at amino acid residues KM 670/671$\rightarrow$NL (of APP770), enhances the production of both A$\beta$1-40 and A$\beta$1-42 (Citron et al., Nature 360:6724. 1992; Lannfelt et al., *Neurosci Lett* 153: 85–7. 1993). The "London" mutation at residue 717, V$\rightarrow$I, G, or F, also results in increased production of A$\beta$ peptide fragments (Schenk et al., *Nature* 400: 173–177. 1999). Several other mutations have been identified, all of which cluster around one of the three secretase cleavage sites in APP, all leading to increased A$\beta$ cleavage.

Many of the therapies contemplated for the treatment of AD target the formation of A$\beta$ peptides by secretase enzyme activity, particularly $\beta$ and $\gamma$ secretases involved in the cleavage of APP into A$\beta$ peptides. Cleavage of APP into A$\beta$ is a natural enzymatic reaction that generates A$\beta$ peptides in areas not associated with the neuronal damage such as basement membrane and arterioles and venules, and areas of the brain not associated with AD pathology. These deposits of A$\beta$ are generally diffuse in nature rather than fibrillary, and A$\beta$ is constitutively secreted by cells throughout life and is found in the cerebrospinal fluid and plasma of all normal individuals (Haas et al., *Nature* 359: 322–5. 1992; Seubert et al., *Nature* 359: 325–7. 1992). These and other data suggest that A$\beta$ aggregation (as opposed to A$\beta$ formation) represents another target for therapeutic intervention.

One recent approach for therapeutic intervention into Alzheimer's Disease and other diseases associated with polypeptide aggregation is treatment with agents that inhibit the nucleation/aggregation of polypeptides. Several screening assays are currently available for the detection of aggregating proteins or aggregating polypeptides involved in various debilitating human diseases.

A unique method for detecting aggregation of proteins is termed Time Resolved Anisotrpy Measurements (TRAMS) (Allsop et al, *Biochem. Biophy. Res. Comm.* 285: 58–63), which measures the movement of fluorescent particles in solution. TRAMS require a mixture of a fluorescently-labeled peptide and non-labeled peptide which are then mixed to the desired concentration, and anisotropy measurements taken over a course of time points. For this particular assay a modified single photon counter with a light emitting diode with a repetition rate of 1 MHz is used for measuring the light emission spectra. Slower movement of the fluorescing particles over time correlates with an increasing number of aggregates. While the TRAMS assay may measure the initial steps in protein aggregation, it is a very complex method of detecting peptide complexes which requires equipment not readily available and involves difficult interpretation of the data.

A scintillation proximity assay (SPA) can also be used to assess aggregation of β-amyloid polypeptides. In the SPA method, three species of β-amyloid$_{1-40}$ are employed, an unlabelled β-amyloid, biotinylated-β-amyloid, and [$^{125}$I]-labeled β-amyloid. A mixture of the three types of peptides are allowed to aggregate at 37° C. for 4 hrs. At this time, 1 mg of streptavidin coated SPA beads (Amersham) are added to the mixture and allowed to incubate for several hours at 37° C, with measurement of $^{125}$I incorporation (into the beads) taken at varying timepoints. To carry out this protocol, large amounts of β1-40 are needed per assay and each assay requires a large amount of time to complete. Thus, this type of assay does not have the high throughput ability needed in the pharmaceutical industry, as well as using potentially hazardous reagents to carry out the protocol.

In the standard Enzyme-Linked Immunosorbant Assay (ELISA) protocol outlined for the detection of α-amyloid aggregation (Howlett et al., FEBS Letters, 417: 249–251. 1997), a polystyrene microtitre plate is coated with a monoclonal antibody to the β-amyloid peptide (e.g. antibody 6E10, Senetek, Napa, Calif.). In a separate microtitre plate, β-amyloid is diluted to a desired concentration in an appropriate buffer and allowed to aggregate overnight in the presence or absence of test compound. After the 24 hr incubation, the aggregation mixture is transferred from the microtitre plate to the p-amyloid antibody coated plate and allowed to bind to antibody. A second, biotinylated 6E10 antibody is then added to the assay plate to bind β-amyloid aggregates. The secondary 6E10 will only be bound if there are β-amyloid molecules present in the assay well bound to other p-amyloid peptides but not to the primary antibody. For detection of the bound biotinylated antibody, Eu3+ labeled streptavidin is added to the wells and detected by excitation at the appropriate wavelength. The amount of Eu3+fluorescence detected will decrease with inhibition of β-amyloid aggregation by the test compound.

While this method is useful in detecting aggregation of β-amyloid peptides, the requirement for peptide-specific monoclonal antibodies limits this assay to availability of the particular antibody and the specificity and binding affinity of the antibody for the peptide.

Berthelier et al, in Anal. Biochem. 295: 227–36. 2001, describe an assay for the detection of polyglutamine aggregate extension where microtiter plate wells are coated with pre-formed polyglutamine aggregates to which are added additional biotinylated-polyglutamine peptides. The rate of incorporation of these newly added peptides is measured using Eu3+labeled-streptavidin to detect bound biotin molecules, corresponding to integrated polyglutamine. This assay, however, does not address whether a test compound affects the prevention of aggregation, or the nucleation event, but rather only provides compounds which modulate continuing polypeptide aggregation.

To this end, Perutz and Windle state in Nature 412: 143–44. 2001, "For any process that occurs on a timescale of years, the controlling step will be nucleation, not growth, and it will occur at random intervals of time."

Thus, there exists a need in the art for improved materials and methods that address the drawbacks of existing protocols designed to detect polypeptide aggregation, and in doing so expedites development of new therapies and reduces the cost of development.

SUMMARY OF THE INVENTION

The present invention relates to materials and methods for determining causes for the initial aggregation, or nucleation, of β-amyloid and other disease inducing aggregating polypeptides, and for delineation of compounds and additional therapies that specifically target polypeptide aggregation and plaque formation in several human disease states. The present invention provides an improved method for identifying compounds which modulate the aggregation of polypeptides, such compounds will be useful in developing therapies for many human disease states characterized by the deleterious aggregation of polypeptides.

For example, the present invention provides a method for identifying modulators of polypeptide aggregation wherein the method comprises: i) providing a substrate attached to a first binding partner, wherein the first binding partner binds with a second binding partner, ii) providing a polypeptide composition comprising polypeptide monomers, wherein at least some of the monomers are modified to comprise to the second binding partner, iii) incubating the polypeptide composition in the presence and absence of a test agent, under conditions in which the polypeptide monomers aggregate into multimers, iv) contacting the polypeptide composition the substrate attached to the first binding partner and v) measuring polypeptide aggregation by detecting polypeptide aggregates bound to the substrate, wherein the detecting comprises measuring the second binding partner, and wherein differential polypeptide aggregation in the presence versus the absence of a test agent identifies the test agent as a modulator compound.

The method can be carried out wherein the incubating step is done either prior to or concurrent with the contacting step.

The first and second binding partners of the invention are molecular pairs that show high binding affinity and specificity for each other and bind to each other very rapidly (relative to the rate at which polypeptide aggregation occurs). At least one must be attachable to a solid substrate and at least one must be attachable to the polypeptide. Exemplary classes of binding partners include high affinity binding small molecules; peptide tags and monoclonal antibodies thereto; fluorophores and monoclonal antibodies thereto; and enzymes and substrates. Exemplary pairs include strepavidin/biotin, anti-Histidine$_6$ (His$_6$-tag) antibodies/His$_6$ peptide tags, anti-biotin/biotin molecules, and anti-glutathione/glutathione tag. In a preferred embodiment, the first and second binding partner pair of the invention are comprised of strepavidin/biotin molecules.

The "first" binding partner is so designated because it is attached to a substrate. The substrate may be any solid support suitable for use in a quantitative assay, such as polymer beads or a solid container such as a polystyrene culture dish. To permit running the assays in a high throughput format, specifically contemplated is a microtiter plate, preferably a 96-well, 384-well or a 1536-well polystyrene microtiter plate, and more preferably a 384-well polystyrene microtiter plate. The first binding partner is attached to the substrate using any suitable techniques such as pre-coating the plate with the first binding partner in an appropriate buffer such as phosphate buffered saline (PBS), magnesium/calcium-free PBS, sodium carbonate, or similar.

The method as described above includes a step of providing a polypeptide composition comprising polypeptide monomers. The polypeptide monomers are unaggregated peptides or polypeptide that can coalesce into aggregates with like polypeptide under physiological conditions. The method is particularly useful when practiced with polypeptides whose aggregates are associated with disease pathogenesis, such as those polypeptides seen to aggregate in Alzheimer's Disease, prion disease, Parkinson's disease, amyotrophic lateral sclerosis (ALS), dialysis-related amyloidosis, corneal dystrophy, and diabetes. Exemplary polypeptides include α-amyloid, Prion protein, α-synuclein, β-2 microglobulin and islet amyloid polypeptide.

The polypeptide composition preferably is comprised of polypeptides whose aggregation correlates a pathologic disease state. Exemplary polypeptide monomers include, but are not limited to, β-amyloid 1-40, β-amyloid 1-42, β-amyloid 1-43, polyglutamine repeats, prion protein (PrP), α-synuclein, or pancreatic amyloid. In a preferred embodiment, the polypeptide of the invention is chosen from amyloid 1-40, β-amyloid 1-42, β-amyloid 1-43, and most preferably is β-amyloid 1-40. Mixtures of different Aβ forms can also be employed. Aggregation of the foregoing polypeptides has been correlated with pathologic states such as Alzheimer's Disease, Down's syndrome, Huntington's chorea, Parkinson's disease, prion disease, Amyotrophic Lateral Sclerosis, Lewy Bodies, or type II diabetes. In a preferred embodiment the pathologic state is chosen from Alzheimer's Disease, Down's syndrome, Lewy Bodies, or type II diabetes. Specifically contemplated by the invention is the assessment of polypeptide aggregation in Alzheimer's disease.

The "polypeptide composition" is formed by mixing polypeptide monomers together in a solution and at a concentration at which aggregation can occur (in the absence of inhibitors). Such solutions and concentrations are easily determined from experience and literature, or alternatively by simple dose-response type analyses to select a concentration at which measurable aggregation occurs at a desirable rate (e.g. in a matter of minutes or hours). Exemplary solutions and concentrations for Aβ range from 2 mg/ml beta-amyloid peptide stock solution in 0.1% acetic acid, to 20–50 μm/ml diluted Aβ peptide in appropriate assay or reaction buffer, containing any or all of the following: Bovine Serum Albumin, milk protein, or similar high molecular weight protein, and mild detergent such as Tween 20, Tween 40, or similar.

In order to perform the method, at least some of the polypeptide monomers are "modified" or chemically coupled to comprise the second binding partner. In other words, the second binding partner is not an epitope or other natural feature of the polypeptide. Instead, the polypeptide is modified to attach the second binding partner. In one variation, the modification comprises expressing a chimeric peptide in which the polypeptide amino acid sequence is modified by attaching an epitope tag such as a His$_6$ tag or Hemagluttinin (HA) tag. In a preferred variation, the polypeptide is modified by chemical reaction e.g., by attaching a biotin molecule to the peptide by conventional techniques. In a preferred embodiment, at least some of the monomers lack the second binding partner.

"Mixing" here may be defined as the incubation in the same plate/well of a solution or suspension of polypeptide monomers that comprise the second binding partner of the invention, optionally with polypeptide monomers which lack the second binding partner. The ratio of monomers having and lacking the second binding partners empirically selected to improve the signal:background measurements of the assay. With respect to Aβ solutions described in the preceding paragraph, a preferred ratio is within the range of 5:1 to 1:1 monomers lacking a second binding partner to monomers comprising the second binding partner, and more preferably wherein the ratio is 2:1 monomers lacking the second binding partner to monomers comprising the second binding partner. This mixing of monomers to form the polypeptide composition may be done in the presence of a test agent or in the absence of a test agent.

The contacting is preferably performed in a liquid environment such as an aqueous buffer, such as magnesium/calcium-free PBS. In one embodiment the polypeptide composition is contacted with the substrate for a time period within the range of 15 minutes to 2 hours, in a preferred embodiment the polypeptide composition is contacted with the substrate for 30 minutes.

The method optionally includes a washing step, wherein the substrate is washed prior to measuring polypeptide aggregation to reduce background measurements caused by unbound polypeptides. Washing of the substrate after incubation of the polypeptide composition and before detection of aggregation is performed in appropriate buffer plus detergent. For example, in a preferred embodiment the wash is performed in magnesium/calcium-free PBS containing mild detergent, and especially contemplated is the use of the mild detergent Tween 20.

The measuring step entails a determination (preferably quantitative) of whether and how much polypeptide aggregate has bound to the substrate, and it involves detecting (measuring) the second binding partner bound (indirectly) to the substrate. In a preferred embodiment the measuring is achieved by contacting the substrate with labeled first binding partner under conditions where the first binding partner will bind to the second binding partner washing the substrate to remove unbound labeled second binding partner, and then measuring the amount of label that remains bound to the substrate. According to this design of the assay, the substrate will bind to polypeptide monomers and/or polypeptide aggregates during the contacting step, due to the affinity of the first binding partner on the substrate for the second binding partner that is present on at least some of the polypeptides. However, unaggregated polypeptide monomers that are bound to the substrate will not be detected during the measuring step because the labeled first binding partner will fail to attach to such monomers (the second binding partner being occupied by the substrate attachment).

In contrast, polypeptide aggregates that include at least two monomers containing second binding partners are detected during the measuring step because only one of the second binding partners is attached to the substrate comprising the first binding partner and at least one of the second binding partners in the aggregate will be unattached and exposed, and thus free to bind the labeled first binding partner in the detecting step. Measuring label that is bound to the substrate thus provides a measurement of aggregation.

The label preferably is detectable and quantifiable at very low concentrations. In preferred embodiments the label attached to the first binding partner is a radionuclide, a fluorophore, a chromophore, and the like. In highly preferred embodiments, the label is chosen from the group consisting of $^{35}S$, $^{125}I$, $^{32}P$, $^3H$, Europium (Eu$^{3+}$) molecules, fluorescein, phycoerythrin, horseradish peroxidase, alkaline phosphotase, and like molecules that demonstrate predictable excitation in detection methods commonly used in the art. Embodiments in which the first binding partner comprises a Europium label are especially preferred.

The method of detection of the label is dependent on the type of label linked to the first binding partner: in one embodiment a radionuclide is detected using scintillation counting, a fluorophore such as fluorescein isothiocyanate (FITC) is detected using the appropriate excitation wavelength, and a chromophore is detected using substrate/enzyme complexes that change color upon mixing and are detected at the appropriate wavelength. In a preferred embodiment a Europium detectable label is detected by excitation at the required wavelength of light and quantitated using methods commonly used in the art.

In one variation, the method of the invention further comprises a step of manufacturing a modulator composition comprising a modulator compound identified as outlined above in a pharmaceutically acceptable carrier. Such a manufacturing step is useful because it permits introducing the modulator into a cell-based assay and/or into a living animal model or human being to evaluate its modulating effects in systems more relevant to efficacy of disease treatment. By "pharmaceutically acceptable carrier" is contemplated any excipient(s), diluent(s), adjuvant(s) or carrier(s) compatible with the modulator composition of the invention and suitable for administration to human or animals. Typically, the carriers, which will be sterile and pyrogen free, will be water, saline, phosphate buffered saline, glucose, or other carriers commonly used in the art to deliver therapeutics.

The method optionally further comprises a step of administering the modulator composition to a mammal, most preferably a human, susceptible to polypeptide aggregation or demonstrating a pathologic state as a result of polypeptide aggregation and determining an improvement in polypeptide aggregation or pathologic state as a result of administration of the modulator composition.

By "administering" is contemplated the introduction of the modulator composition of the invention by any medically-accepted means known in the art to a subject exhibiting an aggregation-induced pathologic state. The modulator composition may be administered via several routes, including but not limited to intravenous injection, subcutaneous injection, intranasal ingestion, oral ingestion, topical administration, and the like. Routes that achieve delivery of the agent to sites of polypeptide aggregation are preferred. Practice of methods of the invention in other mammalian subjects, especially mammals that are conventionally used as models for demonstrating therapeutic efficacy in humans (e.g. primate, porcine, canine, or small rodents such as rabbit, rat and mouse animals), also is contemplated.

By "improvement" in aggregation or pathologic state is contemplated any lessening of detectable polypeptide aggregation, lessening of symptoms of the pathologic state as a result of polypeptide aggregation, such as dementia in Alzheimer's patients, as a result of the administration of the modulator compound. A slowing or arresting of disease progression also is considered an improvement with respect to disease such as Alzheimer's which are known to progress and worsen with time.

In a related aspect the invention provides a kit comprising the materials packaged together in a manner which facilitates their use to practice methods of the invention. In a simplest embodiment, such a kit includes a composition (e.g. substrate, first binding partner, second binding partner, polypeptide monomers, detectable label) packaged in a container such as a sealed bottle or vessel with a label affixed to the container or included in the package that describes use of the composition to practice the method of the invention. In another embodiment, the kit comprises the substrate attached to the first binding partner packaged with the aggregating polypeptide attached to a second binding partner. The kit preferably also includes the first binding partner attached to a detectable label.

Additional features and variations of the invention will be apparent to those skilled in the art from the entirety of this application, and all such features are intended as aspects of the invention.

Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF THE INVENTION

The present invention provides a method for identifying compounds useful in modulating the aggregation of polypeptides involved in the onset of many human disease states. Such compounds are useful in developing therapies for diseases characterized by the aggregation of polypeptides. For instance, a stretch of polyglutamine repeats in a particular protein has been proposed as the cause for many neurological disorders including Huntington's disease and spinal bulbar muscular atrophy, while aggregation of other unrelated proteins are cited as the causes of prion disease (PrP aggregation), Parkinson's disease and amyotrophic lateral sclerosis (ALS) ($\beta$-synuclein aggregation), dialysis-related amyloidosis ($\beta$-2 microglobulin aggregation), corneal dystrophy (kerato-epithelial deposits), aggregation of islet amyloid polypeptide in more than 95% of type II diabetes and $\beta$-amyloid polypeptide aggregation in Alzheimer's Disease.

One advantage of the methods of the present invention is that the rapid method of detecting polypeptide aggregation allows for the rapid assessment of numerous potential modulator compounds. Another advantage of the present invention is that the decreased amount of reagent required per assay reduces cost of the assay per sample.

Figure 1:
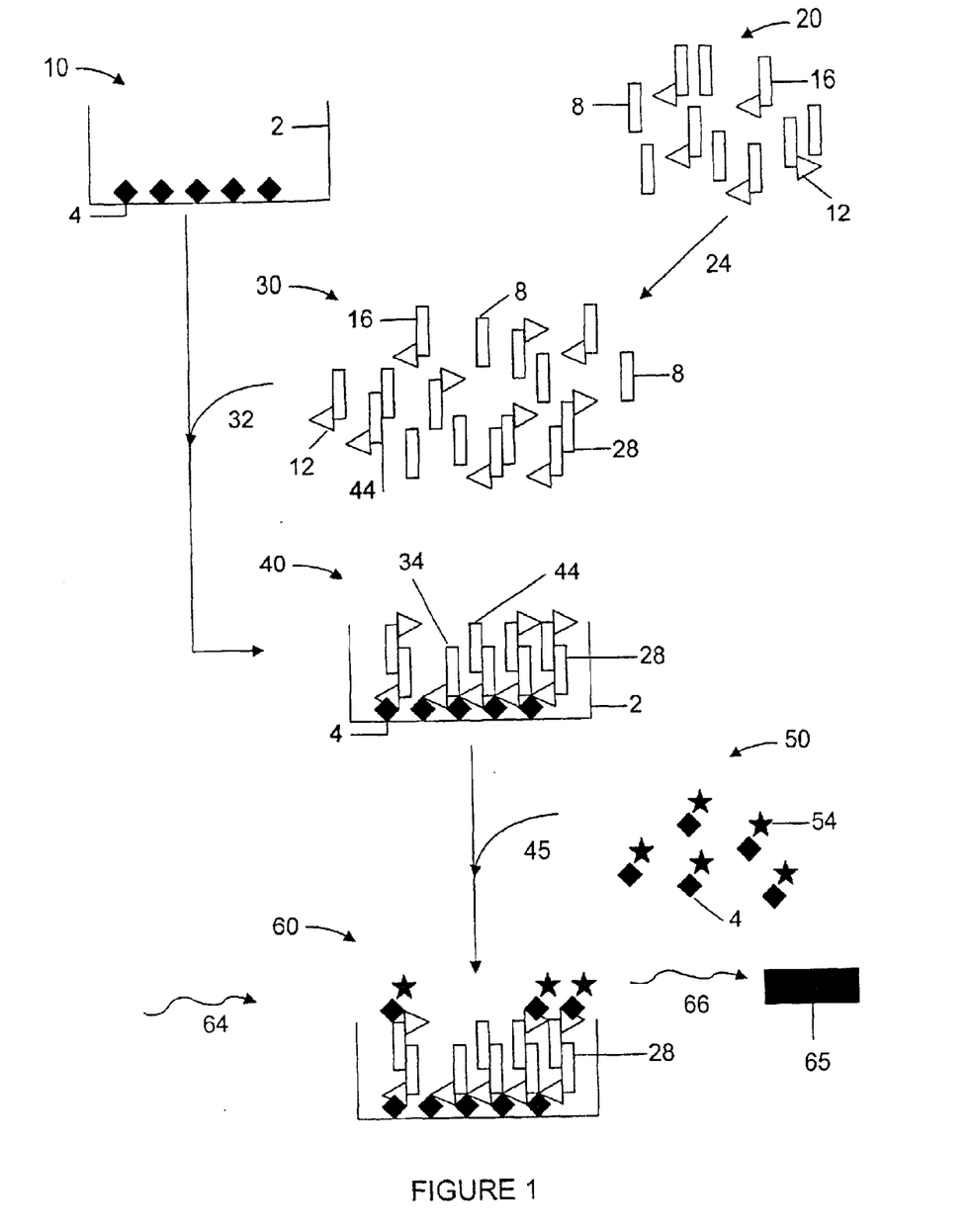
FIG. 1 is a schematic flow diagram illustrating an aggregation assay according to the invention.

An exemplary method of the invention may be carried out as follows and as schematically illustrated in FIG. 1. As depicted in Panel 10, a 96 well polystyrene dish substrate 2 is coated with a first binding partner 4, such as streptavidin, which is provided by incubating the substrate 2 with a solution containing the first binding partner 4, thereby resulting in the coated plate of Panel 10.

As shown in Panel 20, a composition of polypeptide monomers 8, e.g. β-amyloid 1-40 monomers, is provided, e.g. by making a solution in which some of the monomers 16 are linked to a second binding partner 12, an example of which is biotin, which binds to streptavidin. The monomer composition is first incubated 24 in order to allow the monomers to form polypeptide aggregates 28,44 as shown in Panel 30. The incubation 24 is carried out in the presence or absence of a test compound which may modulate, i.e. inhibit or promote, monomer aggregation.

As shown in Panel 30, after the incubation, the polypeptide composition may comprise a variety of species such as polypeptide monomers 8, biotin-linked polypeptide monomers 16 and polypeptide aggregates 28,44. This incubated polypeptide composition is then contacted 32 with the coated plate depicted in 10 comprising the substrate 2 containing the streptavidin first binding partner 4. As depicted in Panel 40, polypeptide species that include at least one biotin molecule will bind to the coated plate of 10 during the contacting step. Molecules from the polypeptide composition bound to the coated plate from Panel 10 may comprise several species of molecules: single polypeptide monomers linked only to the biotin second binding partner 34 and comprising only one streptavidin binding site; aggregated molecules comprising biotinylated polypeptide monomers in association with monomers lacking the second binding partner 44, and therefore also comprising only one stretpavidin binding site; and aggregated monomers comprising biotinylated polypeptide monomers in association with other biotinylated monomers 28, and thus comprising two or more sites for streptavidin 4 binding. Multiple streptavidin binding sites in an aggregated molecule 28 allows for at least one β-amyloid 1-40-biotin to attach to the substrate coated plate 10, while the unoccupied biotin 12 on an associated β-amyloid 1-40-biotin molecule allows for detection of aggregated monomers 28 using a streptavidin first binding partner 4 linked to a detectable label 54, such as Europium$^{3+}$. Monomers 34 that attach to the substrate lack any free biotin.

Polypeptide aggregation is measured by detecting polypeptide aggregates 28 that have bound to the coated plate of 10. The bound aggregated molecules are detected by contacting 45 a detecting agent in 50 (containing the first binding partner 4 linked to a detectable label 54) to the substrate coated plate of 10. As shown in Panel 60, the detecting agent 50 only attaches to substrate-bound, aggregated polypeptides which comprise two or more biotinylated polypeptide monomers 28. Using techniques common in the art, the substrate-bound streptavidin-Eu$^{3+}$50 is detected by excitation of the Eu$^{3+}$ label 54 at an appropriate wavelength 64 and subsequent measurement with a detector 65 of Eu$^{3+}$ fluorescence emitted 66, in units of light absorbance. The degree of Europium$^{3+}$54 excitation measured reflects the amount of detecting agent 50 bound, and thereby correlates with the amount of monomer aggregation occurring during the incubation step 24. Test compounds which result in altered levels of Eu$^{3+}$54 detection when compared to control compounds are considered modulators of polypeptide monomer aggregation.

Figure 2:
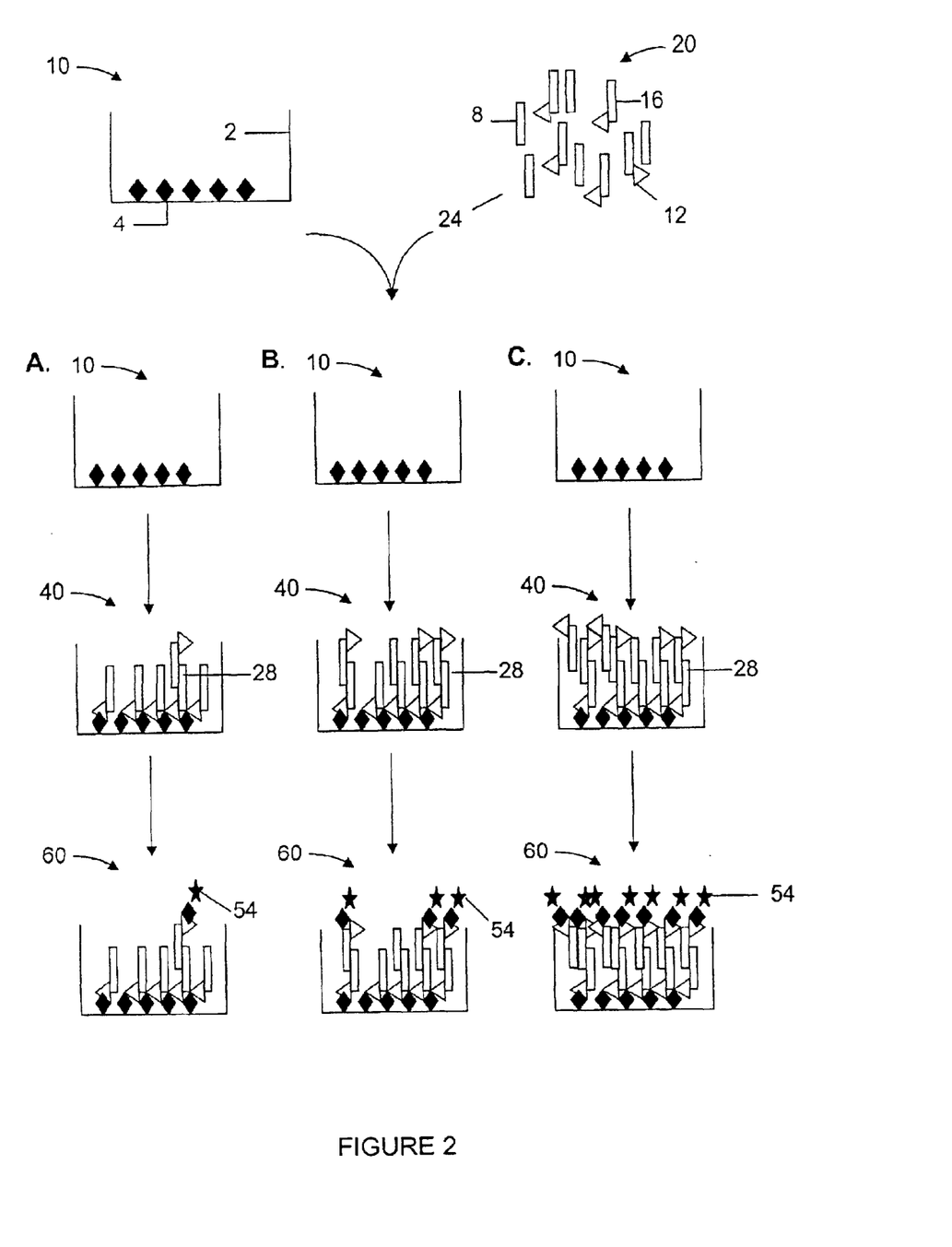
FIG. 2 represents the aggregation assay as performed using test compounds to modulate aggregation.

Using the same symbols and Panels depicted and defined in FIG. 1, FIG. 2 demonstrates three possible outcomes of the aggregation assay dependent upon the test compound added during the incubation step 24. FIG. 2B represents the aggregation shown in FIG. 1, as carried out using control compounds (or buffers only) that do not modulate the natural process of monomer aggregation. FIG. 2A represents aggregation that occurs when a test compound added during the incubation step 24 is an inhibitor of polypeptide aggregation. FIG. 2A, Panel 40 illustrates that inhibition of polypeptide aggregation results in fewer aggregated monomers 28 bound to the substrate coated plate 10. The decrease in aggregated monomers results in less opportunity for the labeled first binding partner 50 to bind to the substrate, as shown in FIG. 2A, Panel 60, thereby lowering the amount of label 54 that is detectable by measurement of Eu$^{3+}$ fluorescence.

FIG. 2C outlines a condition wherein the test agent administered during the incubation step 24 enhances polypeptide aggregation. FIG. 2C, Panel 40 demonstrates that promotion of polypeptide monomer aggregation results in an increase in aggregated monomers 28 bound to the substrate coated plate 10. The enhancement of polypeptide aggregation results in a greater amount of labeled first binding partner 50 attached to the free second binding partner on the aggregated monomers 28, as represented in FIG. 2C, Panel 60. Increased aggregation and subsequent increased binding of the labeled first binding partner 50 leads to augmented detectable label 54 bound to the substrate, resulting in amplification of Eu$^{3+}$signal emitted compared to control compounds, thus providing a quantitative measure of the capacity of a test compound to modulate polypeptide monomer aggregation.

The aggregating polypeptides used in the invention, wherein "aggregating" is defined as the binding of polypeptide monomers to each other forming a higher order molecular structure, include polypeptides known to be associated with human disease states. In a preferred invention the polypeptides can be chosen from the group consisting of: β-amyloid polypeptides comprised of any peptide resulting from beta-secretase cleavage of APP, especially considered are β-amyloid 1-39, β-amyloid 1-40, β-amyloid 1-41, β-amyloid 1-42, and β-amyloid 1-43; polyglutamine repeats of at least 27 glutamine residues to as many as 45 glutamine repeats, and most preferably of 38 glutamine residues; α-synuclein peptides of at least 11 amino acids comprised of the common 11 residue repeat found in α-synuclein; prion protein, and pancreatic amyliod peptides (ranging from 6 to 37 amino acids in length) wherein the peptide includes the sequence NFGAIL (Azriel et al., *J. Biol. Chem.* 276: 34156–161. 2001).

The first binding partner of the invention and the second binding partner of the invention, selected from molecular pairs that show high affinity of binding to each other and are easily applicable to many different polypeptides, may be chosen from the group including but not limited to strepavidin/biotin, anti-Histidine$_6$ (His$_6$-tag) antibodies/His$_6$ peptide tags, anti-biotin/biotin molecules. The first binding partner can be chosen from, but is not limited to, the group consisting of streptavidin, anti-His$_6$ antibodies, anti-myc tag, anti-hemagluttin, anti-fluorophore (e.g. anti-fluorescein isothiocyanate), anti-biotin, and the like.

The second binding partner of the invention can be chosen from the group consisting of but not limited to biotin molecules, alkaline phosphatase, fluorophores, genetically engineered peptide tags such as a histadine His$_6$ tag linked to the aggregating polypeptide, a myc-tag, Hemagluttinin tags, and the like. Biotin, fluorophores, and other contemplated small molecules comprising the second binding partner can be linked to the polypeptide of the invention by means well-known in the art such as a commercially produced Biotinylation kit (Sigma, St. Louis, Mo.), or alternative methods commonly used in organic chemistry to chemically attach a small molecule to a peptide or protein (see e.g., Current Protocols in Protein Chemistry, John Wiley & Sons, 2001). Genetically engineered tags, e.g., $His_6$ and myc-tags, are operably linked to the polypeptide of the invention using standard recombinant DNA methods well known in the art (see e.g., Current Protocols in Molecular Biology, John Wiley & Sons, 2001), or using conventional peptide synthesis techniques.

In a preferred embodiment, the first and second binding partner pair of the invention are comprised of strepavidin/biotin molecules.

The first binding partner of the invention is attached to a substrate of the invention. The substrate of the invention may be any material or substance appropriate for performing the present method, such as polymer beads or a solid container such as a polystyrene culture dish, specifically contemplated is a polystyrene microtiter plate, preferably a 96-well, 384-well or 1536-well polystyrene microtiter plate, and more preferably a 384-well polystyrene microtiter plate. The first binding partner is attached to the substrate in an appropriate buffer such as phosphate buffered saline (PBS), magnesium/calcium-free PBS, sodium carbonate, or similar.

For measuring polypeptide aggregation, the first binding partner can be operably linked to a label, wherein the label is a detectable label, and preferably is detectable and quantifiable at very low concentrations. In a preferred embodiment the label attached to the first binding partner can be either a radionuclide, a fluorophore, a chromophore, and the like. In a more preferred embodiment, the label is chosen from the group consisting of $^{35}S$, $^{125}I$, $^{32}H$, europium ($Eu^{3+}$) molecules, fluorescein, phycoerythrin, horseradish peroxidase, alkaline phosphotase, and like molecules that demonstrate predictable excitation in detection methods commonly used in the art.

The test agent employed in the method of the invention can be any organic or inorganic chemical or biological molecule that one would want to test for the ability to modulate polypeptide aggregation. Since the most preferred test agents are those that can be administered as therapeutics, it will be apparent that molecules with limited toxicity are preferred. However, toxicity can be screened in subsequent assays and often "designed out" of molecules by pharmaceutical chemists. Screening of chemical libraries such as those customarily kept by pharmaceutical companies, consisting of both chemically synthesized and natural compounds, and combinatorial libraries, is specifically contemplated.

Chemical libraries may contain known compounds, proprietary structural analogs of known compounds, or compounds that are identified from natural product screening.

Natural product libraries are collections of materials isolated from natural sources, typically, microorganisms, animals, plants, or marine organisms. Natural products are isolated from their sources by fermentation of microorganisms followed by isolation and extraction of the fermentation broths or by direct extraction from the microorganisms or tissues (plants or animal) themselves. Natural product libraries include polyketides, non-ribosomal peptides, and variants (including non-naturally occurring variants) thereof. For a review, see Cane et al., *Science*, 282, 63–68 (1998).

Combinatorial libraries are composed of large numbers of related compounds, such as peptides, oligonucleotides, or other organic compounds as a mixture. Such compounds are relatively straightforward to design and prepare by traditional automated synthesis protocols, PCR, cloning or proprietary synthetic methods. Of particular interest are peptide and oligonucleotide combinatorial libraries.

Still other libraries of interest include peptide, protein, peptidomimetic, multiparallel synthetic collection, recombinatorial, and polypeptide libraries. For a review of combinatorial chemistry and libraries created thereby, see Myers, *Curr. Opin. Biotechnol.*, 8, 701–707 (1997).

Modulator compounds identified by assessment of the test agents may be formulated into compositions which include pharmaceutically acceptable (i.e., sterile and non-toxic) liquid, semisolid, or solid diluents that serve as pharmaceutical vehicles, excipients, or media. Modulators formulated in this manner can be further screened for modulating activity in vivo, e.g., in animal models for disease; or can be administered to humans in clinical trials; or can be made and sold as pharmaceuticals. Modulator compositions according to the invention may be administered in any suitable manner using an appropriate pharmaceutically-acceptable vehicle, e.g., a pharmaceutically-acceptable diluent, adjuvant, excipient or carrier. The composition to be administered according to methods of the invention preferably comprises a pharmaceutically-acceptable carrier solution such as water, saline, phosphate-buffered saline, glucose, or other carriers conventionally used to deliver therapeutics.

The modulator compositions can be packaged in forms convenient for delivery. The compositions can be enclosed within a capsule, caplet, sachet, cachet, gelatin, paper, or other container. The dosage units can be packaged, e.g., in tablets, capsules, suppositories or cachets.

The modulator compositions identified by the invention may also be introduced into the subject being treated for a pathological disease state as a result of polypeptide aggregation by any conventional method including, e.g., by intravenous, intradermal, intramuscular, intracerebral, intraperitoneal, or subcutaneous injection; by oral, transdermal, sublingual, intranasal, anal, or vaginal, delivery. The treatment may consist of a single dose or a plurality of doses over a period of time. Dosing will be determined by standard dose-response studies, first in animal models and then in clinical testing, revealing optimal dosages for particular disease states and patient populations. The amounts of modulator composition in a given dose will vary according to the size of the individual to whom the therapy is being administered, generally on a mg/kg basis, as well as the characteristics of the disorder being treated.

The method of the invention will be more readily understood by reference to the following examples, which are provided as a manner of illustration and are not intended to be limiting.

EXAMPLE 1

Time Resolved Fluorescence Assay For β-Amyloid Polypeptide Aggregation

The following example is an embodiment of the invention which demonstrates a method for identifying modulators of β-amyloid polypeptide aggregation. β-amyloid polypeptide monomers in solution in vitro are pre-disposed toward aggregation of the peptide monomers into larger, multimeric molecules. Aggregation of the β-amyloid monomers in vivo is a primary contributor to neuronal damage in Alzheimer's Disease. The present invention allows for a sensitive in vitro analysis of β-amyloid aggregation and the effects of outside compounds or test agents on the extent of β-amyloid peptide aggregate formation.

Beta-amyloid 1-40 (Aβ) and biotin-labeled β-amyloid 1-40 peptides were purchased from Biosource (Camarillo, Calif.). β-amyloid and biotinylated amyloid stock solutions, diluted in 0.1% acetic acid and corrected for 80% peptide content, were diluted to 83 μg/ml and 42 μg/ml, respectively, in reaction buffer (Dulbecco's PBS pH 7.4, 0.02% Tween 20). An equal mixture of the two β-amyloid products was then brought to a final concentration of 62.5 μg/ml total β-amyloid, giving a final 2:1 ratio of unbiotinylated to biotinylated Aβ polypeptide. When analyzing aggregation in the presence of test compound, 5 ul of diluted test compound (120 uM in 10% DMSO) was added to each well being analyzed in a 384-well polystyrene plate (Nunc). Test compounds are added over a range of concentrations. Twenty microliters of the β-amyloid reaction mixture was dispensed into each well of the 384 well plate, giving the final assay conditions as 24 uM test compound, 2% DMSO, and 50 ug/ml β-amyloid in a final volume of 25 uL. Plates were then sealed with foil sealers (Corning), and incubated at 37° C. for 24 hrs.

After 24 hrs, 35 uL of reaction buffer was added to a streptavidin coated plate using a Multidrop pipettor. Using a multipette, 14 uL of the aggregation assay plate media, now containing either aggregated or monomeric Aβ, resulting from incubation with the test agent, was added to the streptavidin coated plate containing 35 uL of buffer. Plates were incubated 30 min at room temperature, washed three times with reaction buffer (90 uL/wash), and 50 uL/well of Eu3+labeled streptavidin (250 ng/ml, Wallac,/Perkin Elmer Life Sciences, Boston, Mass.) in DELFIA assay buffer (Wallac) added to assay wells and incubated 2 hr at room temperature. Plates were washed with reaction buffer and 75 uL of DELFIA Enhancement solution (Wallac) was added to each well and the plates read on TRF capable plate reader (excitation at 337 run and emission at 620 nm).

Results of the TRF aggregation assay demonstrate that the addition of test compounds such as known Aβ aggregation inhibitors ApoE3 or QKLVFF peptide (Lowe et al., *Biochemistry* 40: 7882–89. 2001)(Bachem Bioscience, Philadelphia, Pa.) prevents Aβ aggregation by 75% and 44%, respectively. Further screening with a priority compound library shows Aβ aggregation inhibited by greater than 90% compared to control wells lacking test compound. The background of this TRF assay is less than 0.7% of total $Eu^{3+}$ absorbance observed for positive control wells. Thus, this highly sensitive TRF aggregation assay proves an effective method for identifying compounds that prevent Aβ aggregation at either high or moderate levels of inhibition.

EXAMPLE 2

Comparison of TRF Assay to Standard ELISA Potocol

For the β-amyloid aggregation ELISA protocol (Howlett et al., *supra*), 96 uL diluted β amyloid solution (51 μg/ml) is added to a 96-well polystyrene plate in the presence of and absence of 2 μL of an aggregation inhibitor test compound diluted in DMSO. The Aβ is incubated overnight to allow for aggregation and an aliquot transferred to another 96-well polystyrene plate, precoated with anti-Aβ antibody (6E10, Senetek, Napa, Calif.) overnight, washed, and blocked with Dulbecco's PBS/1% BSA solution. After 3–4 hours, the plates were washed and a secondary anti-Aβ antibody demonstrating the same specificity as the coating antibody but biotinylated (6E10-bio) was added to the plate. The secondary, biotinylated antibody was bound with 200 μL $Eu^{3+}$-streptavidin (100 ng/ml) in DELFIA assay buffer, the excess washed off, and the plate developed in DELFIA enhancement solution and read on a TRF plate reader as outlined above.

Analysis of the absorbance of the fluorophore in the ELISA showed that the background absorbance is anywhere from 1.3%, 2%, to 13% of the positive control wells, much greater than the background seen in the TRF aggregation assay and shows greater inconsistentcy. In addition, the ELISA assay only provides for approximately 1.5 times greater detection of Aβ aggregates over the addition of fresh Aβ peptide to the antibody coated plate (used as a background reading), indicating that the assay was less sensitive than the TRF assay in detecting Aβ aggregates. Inhibition of Aβ aggregation in the ELISA by known Aβ inhibitor rifampicin showed ~30% inhibition of Aβ aggregation as compared to almost complete inhibition seen in the TRF assay by alternate test compounds. This may indicate that the sensitivity of the ELISA is less than the present TRF assay and therefore smaller changes in aggregation are more difficult to detect by ELISA Thus, use of the presently disclosed TRF assay for detecting aggregates of polypeptide aggregation is a more sensitive assay than the current methods of aggregate detection practiced in the art.

EXAMPLE 3

Improved Rate of Detection of Modulators of β-amyloid Nucleation and Aggregation Coupling of the TRF-Assay described above with a turbidity, or optical density, assay can vastly improve the ability to detect modulators of β-amyloid nucleation and aggregation. A turbidity assay measures the onset of aggregation, or nucleation, of aggregating proteins. A nucleation event is characterized by a considerable lag time in the appearance of aggregates precipitating out of assay solution and giving off an optical density (OD) reading, followed by a rapid increase in OD due to acceleration of aggregation.

A test compound that has been determined to modulate β-amyloid aggregation in the TRF assay can also be assayed in an optical density assay (Findeis et al, *Biochemistry* 38: 6791–6800. 1999; and WO98/08868) to verify if the compound is involved with nucleation of β-amyloid aggregates, or if the compound only inhibits β-amyloid aggregation after the initial seeding of aggregates has occurred.

For the turbidity assay, test compound suspended in 100% DMSO or 5 uL of 100% DMSO is added to 96 well or 384 well untreated, clear polystyrene plates (Corning). β-Amyloid is dissolved in 0.1% acetic acid to a 20× concentration (1.02 mM) correcting for peptide content and then diluted to 51 uM in assay buffer (10 mM Sodium phosphate, 100 mM NaCl, pH 7.4). Diluted peptide is added to the test compound in a volume of 245 uL, giving the final assay conditions as 50 uM β-amyloid peptide in 250 uL volume, with 2% DMSO. Turbidity of the solution is quantitated by determining the optical density at 405 nm. Using an appropriate plate reader (i.e. Spectramax) optical density readings are made at 10 minute intervals. Between time intervals the plate is placed on a plate shaker (4.2 setting, 800 rpm) at room temperature. Increasing OD readings indicate aggregation of beta-amyloid in solution. OD readings taken in the presence and absence of test compound will indicate whether the test compound is an inhibitor (decreased OD reading compared to positive control) of β-amyloid aggregation and more specifically of β-amyloid nucleation (increased lag time between start of assay and appearance of turbid solution mixture).

With the present TRF assay of the invention, up to 352 test agents can be screened in one assay. This initial large screening capability of the current TRF assay coupled with the turbidity assay allows for a more efficient and expedient determination of viable modulators of polypeptide aggregation. Therefore, the presently disclosed TRF analysis method provides a significant savings in time required to complete an aggregation assay, decreases the amount of reagent used by the assay, and subsequently saves cost by using less reagent per assay and speeding up analysis of potentially important therapeutics in Alzheimer's and many other pathogenic states induced by aggregating polypeptides.

EXAMPLE 4

Novel TRF Assay Useful to Detect Many Species of Aggregating Polypeptides

The above TRF assay can be utilized to detect aggregation of polypeptides of many different proteins of interest (PrP, α-synucleiens, islet amyloid-β, β, β-2 microglobulin), making it a highly adaptable, useful technique in the art. In the presently disclosed TRF assay, use of the streptavidin/biotin molecular pairing or other high-affinity binding molecules wherein one of the binding partners is chemically or recombinantly linked to the peptide of interest, allows for the method of the invention to be adapted to any of the aforementioned proteins or polypeptides. The standard ELISA protocol commonly used in the art is not as useful for such adaptation as it requires antigen-specific antibodies for the assessment of polypeptide aggregation. Thus, use of an ELISA for detection of polypeptide aggregation is limited by what polypeptide-specific reagents are available at the time for conducting the assay.

For example, a substrate is initially coated with the first binding partner, e.g. streptavidin, as outlined previously. An amount of peptide or protein of interest (e.g. α-synuclein or prion protein) is biotinylated using standard methods (e.g. commercial biotinylation kit, Sigma) and the biotinylated and unbiotinylated protein of interest allowed to aggregate in the presence or absence of a test compound as outlined in EXAMPLE 1. The polypeptide composition of interest is then incubated on the substrate with the first binding partner attached to a detectable label as outlined in Example 1 and the test compound assessed for it's ability to modulate, i.e. stimulate or inhibit, the aggregation of the assayed protein or polypeptide based on the amount of detectable label measured in the assay. In this manner, aggregation and inhibitors of aggregation can be assessed for a wide variety of proteins.

EXAMPLE 5

Formulation of a TRF-Assay Kit

The invention can also be packaged in a kit for rapid screening of polypeptide aggregation, comprising one or more compounds or compositions of the invention. In a simplest embodiment, such a kit includes a compound or composition described herein as useful for practice of a method of the invention (e.g., reagents for labeling a protein or polypeptide with biotin molecules), packaged in a container such as a sealed bottle or vessel, with a label affixed to the container or included in the package that describes use of the compound or composition to practice the method of the invention. In a more specific embodiment, the kit would include unlabeled and biotinylated polypeptides (e.g., amyloid-$β_{1-40}$ and/or A-$β_{1-42}$ polypeptides) for use in the screening assay. The kit may further include a microtitre plate for use with the invention, either 96 well or 384 well, pre-coated with streptavidin for the binding of biotinylated polypeptides made by or included in the kit, as well as the optimal level of detecting agent, $Eu^{3+}$-streptavidin, designed to detect the biotinylated compound of the invention. The kit as packaged optionally will also contain a positive control modulator compound in order to compare detection of aggregates in the presence of a test agent with the detection of aggregates in the presence of the positive control compound, and determine the efficacy of the test agent as a modulator of polypeptide aggregation.

It will be clear that the invention may be practiced otherwise than as particularly described in the foregoing description and examples. Numerous modifications and variations of the present invention are possible in light of the above teachings and, therefore, are within the scope of the invention.

We claim:

1. A method for identifying modulators of β-amyloid aggregation comprising:
   i) providing a substrate attached to streptavidin, wherein the streptavidin binds with biotin;
   ii) providing a polypeptide composition comprising β-amyloid monomers, wherein at least some of the β-amyloid monomers are modified to comprise biotin;
   iii) incubating the polypeptide composition in the presence and absence of a test agent, under conditions in which the β-amyloid monomers aggregate into multimers;
   iv) contacting the polypeptide composition to the substrate attached to the streptavidin under conditions wherein biotin binds to streptavidin; whereby β-amyloid or multimers that comprise biotin bind to the streptavidin of the substrate;
   v) contacting the substrate with a detecting agent comprising the streptavidin, wherein the detecting agent binds to biotin on β-amyloid aggregates that are bound to the substrate; and
   vi) measuring β-amyloid aggregation by detecting the detecting agent bound to β-amyloid aggregates bound to the substrate, wherein differential β-amyloid aggregation measurements in the presence versus the absence of a test agent identifies the test agent as a modulator of β-amyloid aggregation.

2. A method according to claim 1 wherein the monomers are selected from the group consisting of β-amyloid 1-40, β-amyloid 1-42, β-amyloid 1-43, and mixtures thereof.

3. A method according to claim 1 wherein the β-amyloid aggregation correlates with a pathologic disease state.

4. A method according to claim 3 wherein the pathologic state is a member of the group consisting of Alzheimer's Disease and Down's syndrome.

5. A method for identifying modulators of polyglutamine repeat containing protein aggregation comprising:
   i) providing a substrate attached to streptavidin, wherein the streptavidin binds with biotin;
   ii) providing a polypeptide composition comprising polyglutamine repeat containing protein monomers, wherein at least some of the polyglutamine repeat containing protein monomers are modified to comprise biotin;

iii) incubating the polypeptide composition in the presence and absence of a test agent, under conditions in which the polyglutamine repeat containing protein monomers aggregate into multimers;

iv) contacting the polypeptide composition to the substrate attached to the streptavidin under conditions wherein biotin binds to streptavidin; whereby polyglutamine repeat containing protein or multimers that comprise biotin bind to the streptavidin of the substrate;

v) contacting the substrate with a detecting agent comprising the streptavidin, wherein the detecting agent binds to biotin on polyglutamine repeat containing protein aggregates that are bound to the substrate; and vi) measuring polyglutamine repeat containing protein aggregation by detecting the detecting agent bound to polyglutamine repeat containing protein aggregates bound to the substrate, wherein differential polyglutamine repeat containing protein aggregation measurements in the presence versus the absence of a test agent identifies the test agent as a modulator of polyglutamine repeat containing protein aggregation.

6. A method according to claim 5 wherein aggregation of the polyglutamine containing polypeptide correlates with a pathologic disease state.

7. A method according to claim 6 wherein the pathologic state is a member of the group consisting of Huntington's disease and spinal bulbar muscular atrophy.

* * * * *

UNITED STATES PATENT AND TRADEMARK OFFICE
CERTIFICATE OF CORRECTION

PATENT NO. : 6,846,640 B2
DATED : January 25, 2005
INVENTOR(S) : Matthew L. Peach et al.

It is certified that error appears in the above-identified patent and that said Letters Patent is hereby corrected as shown below:

Title page, Item [54] and Column 1, line 3,
Title, please insert -- β -- before "[BETA]"

Title page,
Item [56], References Cited, OTHER PUBLICATIONS, "Hughes et al.," reference, please delete "β2" and insert -- α2 --

Column 2,
Line 30, please delete "6724." and insert -- 627-4. --
Line 60, please delete "Anisotrpy" and insert -- Anisotropy --

Column 3,
Line 27, please delete "α-amyloid" and insert -- β-amyloid --
Lines 36 and 41, please delete "p-amyloid" and insert -- β-amyloid --

Column 5,
Line 12, please delete "α-amyloid" and insert -- β-amyloid --
Line 21, please insert -- β- -- before "amyloid"
Line 47, please delete "20" and insert -- 20 --
Line 47, please delete "40" and insert -- 40 --

Column 6,
Line 27, please delete "20" and insert -- 20 --
Line 64, please delete "phosphotase" and insert -- phosphatase --

Column 8,
Line 58, please delete "β-synuclein" and insert -- α-synuclein --

Column 9,
Line 5, please delete "96" and insert -- 96 --

Column 11,
Line 36, please delete "$^{32}$H" and insert -- $^{32}$P, $^{3}$H, --
Line 38, please delete "phosphotase" and insert -- phosphatase --

Column 13,
Line 12, please delete "20" and insert -- 20 --
Line 34, please delete "Eu3+" and insert -- $Eu^{3+}$ --
Line 57, please delete "Potocol" and insert -- Protocol --

UNITED STATES PATENT AND TRADEMARK OFFICE
CERTIFICATE OF CORRECTION

PATENT NO. : 6,846,640 B2
DATED : January 25, 2005
INVENTOR(S) : Matthew L. Peach et al.

It is certified that error appears in the above-identified patent and that said Letters Patent is hereby corrected as shown below:

<u>Column 14,</u>
Line 26, please delete "ELISA" and insert -- ELISA. --

<u>Column 15,</u>
Line 28, please delete "α-synucleiens" and insert -- α-synucleins --
Line 28, please delete "amyloid-β, β," and insert -- amyloid-β --

Signed and Sealed this

Twenty-first Day of June, 2005

JON W. DUDAS
*Director of the United States Patent and Trademark Office*